US008108052B2

(12) United States Patent
Boling

(10) Patent No.: US 8,108,052 B2
(45) Date of Patent: Jan. 31, 2012

(54) PERCUTANEOUS LEADS WITH LATERALLY DISPLACEABLE PORTIONS, AND ASSOCIATED SYSTEMS AND METHODS

(75) Inventor: C. Lance Boling, San Jose, CA (US)

(73) Assignee: Nervo Corporation, Menlo Park, CA (US)

( * ) Notice: Subject to any disclaimer, the term of this patent is extended or adjusted under 35 U.S.C. 154(b) by 628 days.

(21) Appl. No.: 12/129,078

(22) Filed: May 29, 2008

(65) Prior Publication Data
US 2009/0299444 A1   Dec. 3, 2009

(51) Int. Cl.
*A61N 1/00* (2006.01)
(52) U.S. Cl. .......................... 607/118; 607/116; 607/117
(58) Field of Classification Search .................. 607/122, 607/116–119
See application file for complete search history.

(56) References Cited

U.S. PATENT DOCUMENTS

| | | | |
|---|---|---|---|
| 3,724,467 A | 4/1973 | Avery et al. | |
| 4,379,462 A | 4/1983 | Borkan et al. | |
| 5,003,992 A * | 4/1991 | Holleman et al. | 607/120 |
| 5,119,832 A | 6/1992 | Xavier | |
| 5,129,404 A | 7/1992 | Spehr et al. | |
| 5,179,962 A | 1/1993 | Dutcher et al. | |
| 5,251,634 A | 10/1993 | Weinberg | |
| 5,336,182 A | 8/1994 | Lundquist et al. | |
| 5,354,326 A | 10/1994 | Comben et al. | |
| 5,392,791 A | 2/1995 | Nyman et al. | |
| 5,480,421 A * | 1/1996 | Otten | 607/122 |
| 5,641,326 A | 6/1997 | Adams | |
| 5,733,322 A | 3/1998 | Starkebaum | |
| 5,741,319 A | 4/1998 | Woloszko et al. | |
| 5,824,030 A | 10/1998 | Yang et al. | |
| 5,871,531 A | 2/1999 | Struble | |
| 6,024,702 A | 2/2000 | Iversen | |
| 6,895,283 B2 | 5/2005 | Erickson et al. | |
| 7,107,097 B2 | 9/2006 | Stern et al. | |
| 7,146,222 B2 | 12/2006 | Boling | |
| 2002/0128700 A1 | 9/2002 | Cross | |

(Continued)

FOREIGN PATENT DOCUMENTS

GB   2449546 A   11/2008

(Continued)

OTHER PUBLICATIONS

International Search Report and Written Opinion; International Patent Application No. PCT/US09/045678, Applicant: Nevro Corporation, mailed Aug. 13, 2009, 18 pages.

(Continued)

*Primary Examiner* — Niketa Patel
*Assistant Examiner* — Catherine Voorhees
(74) *Attorney, Agent, or Firm* — Perkins Coie LLP

(57) ABSTRACT

Percutaneous leads with laterally displaceable sections, and associated systems and methods are disclosed. A device in accordance with a particular embodiment includes a lead body that in turn includes first, second and third percutaneous portions. The first portion can carry an electrical contact, the second portion can be spaced apart from the first portion, and the third portion can be positioned between the first and second portions along a deployment axis. The third portion can have a stiffness in a direction transverse to the deployment axis that is less than a stiffness of both the first and second portions transverse to the deployment axis, and a diameter that is less than corresponding diameters of the first and second portions.

19 Claims, 6 Drawing Sheets

U.S. PATENT DOCUMENTS

| | | |
|---|---|---|
| 2003/0125786 A1 | 7/2003 | Gliner et al. |
| 2005/0234318 A1 | 10/2005 | Schulman et al. |
| 2005/0251237 A1 | 11/2005 | Kuzma et al. |
| 2006/0030918 A1 | 2/2006 | Chinn et al. |
| 2006/0089691 A1 | 4/2006 | Kaplan et al. |
| 2007/0073353 A1 | 3/2007 | Rooney et al. |
| 2007/0239249 A1 | 10/2007 | Tockman et al. |
| 2007/0255364 A1 | 11/2007 | Gerber et al. |
| 2007/0261115 A1 | 11/2007 | Gerber et al. |
| 2008/0183257 A1* | 7/2008 | Imran et al. .................. 607/117 |
| 2009/0024075 A1* | 1/2009 | Schroeppel et al. ............ 604/20 |
| 2009/0222073 A1* | 9/2009 | Flowers et al. ............... 607/116 |
| 2009/0319013 A1 | 12/2009 | Boling et al. |
| 2010/0137955 A1 | 6/2010 | Milijasevic et al. |
| 2010/0274314 A1 | 10/2010 | Alataris et al. |
| 2010/0274336 A1 | 10/2010 | Nguyen-Stella et al. |
| 2011/0071604 A1* | 3/2011 | Wahlstrand et al. .......... 607/116 |

FOREIGN PATENT DOCUMENTS

| | | |
|---|---|---|
| WO | WO-2008094952 | 8/2008 |

OTHER PUBLICATIONS

Medtronic, "Physician and Hospital Staff Manual," InterStrim System, Neurological Division. 21 pages, 1999.

Medtronic, "Physician and Hospital Staff Manual—InterStim System: Model 3023 Quadripolar Neurostimulator, Model 3886 Lead, Model 3080 Lead, Model 3095 Extension" and "Patient Manual—InterStim Therapy for Urinary Control," Neurological Division, Medtronic Inc. 1999, 93 pages.

* cited by examiner

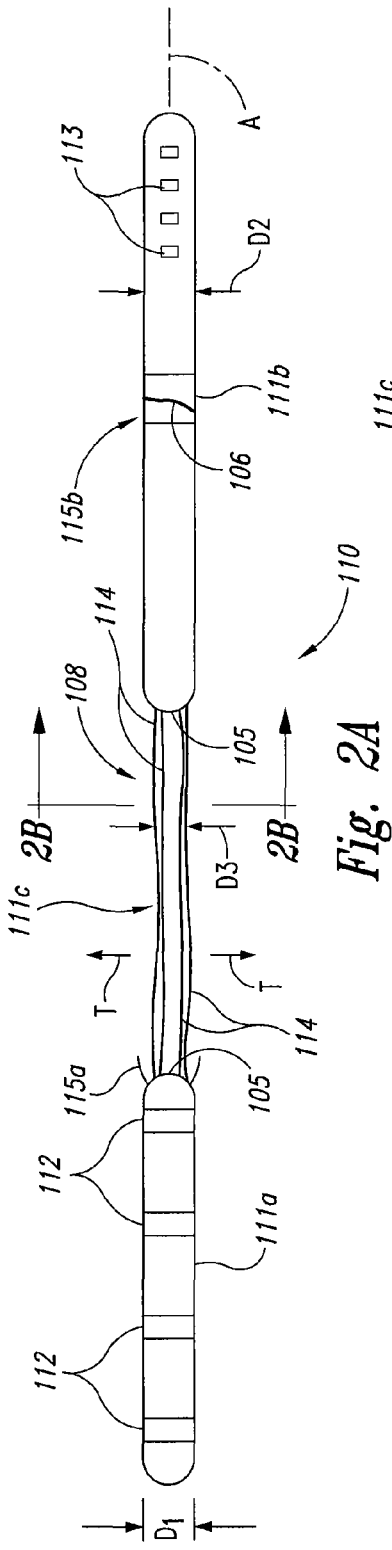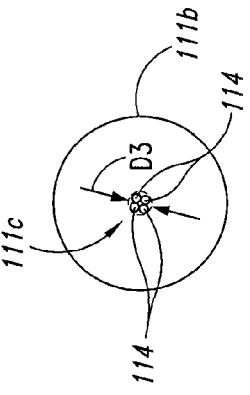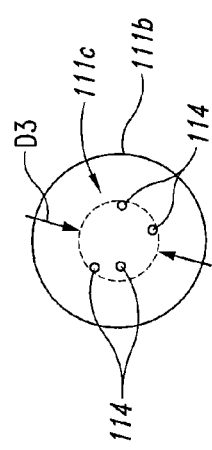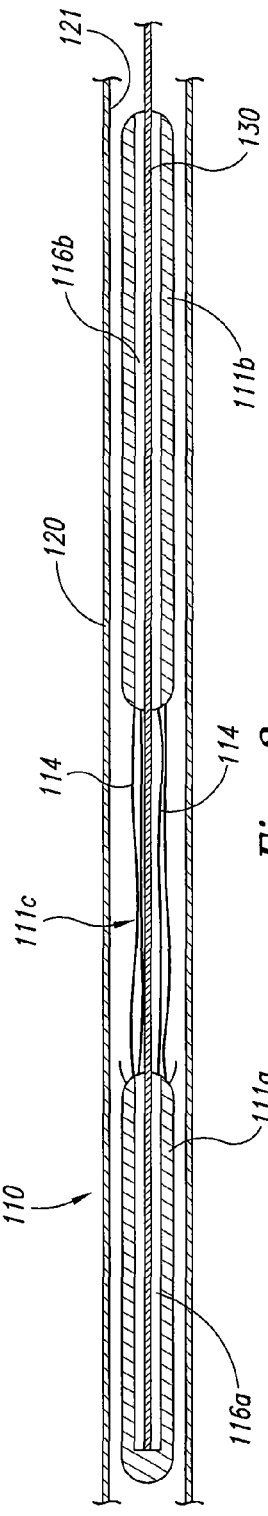

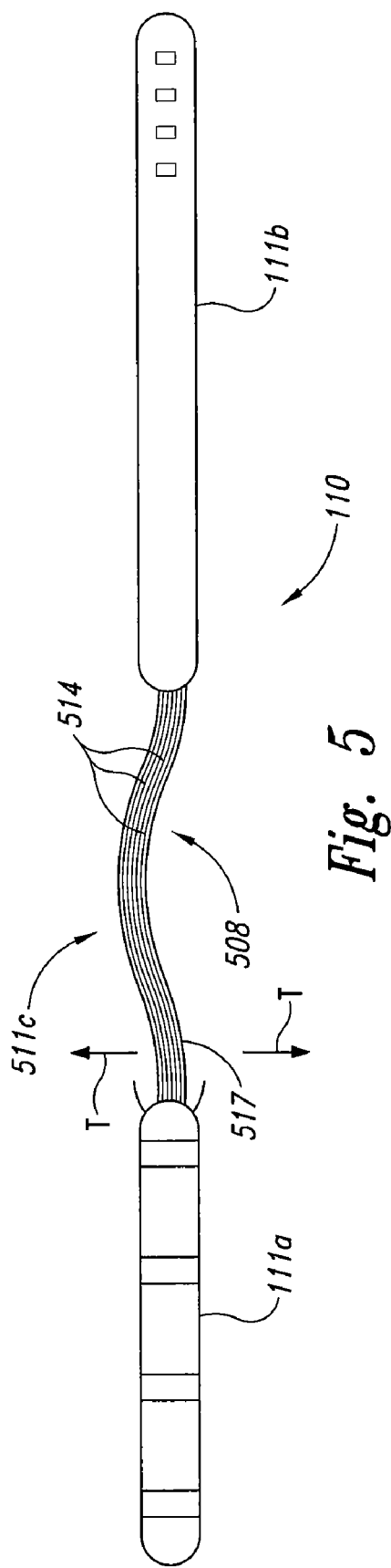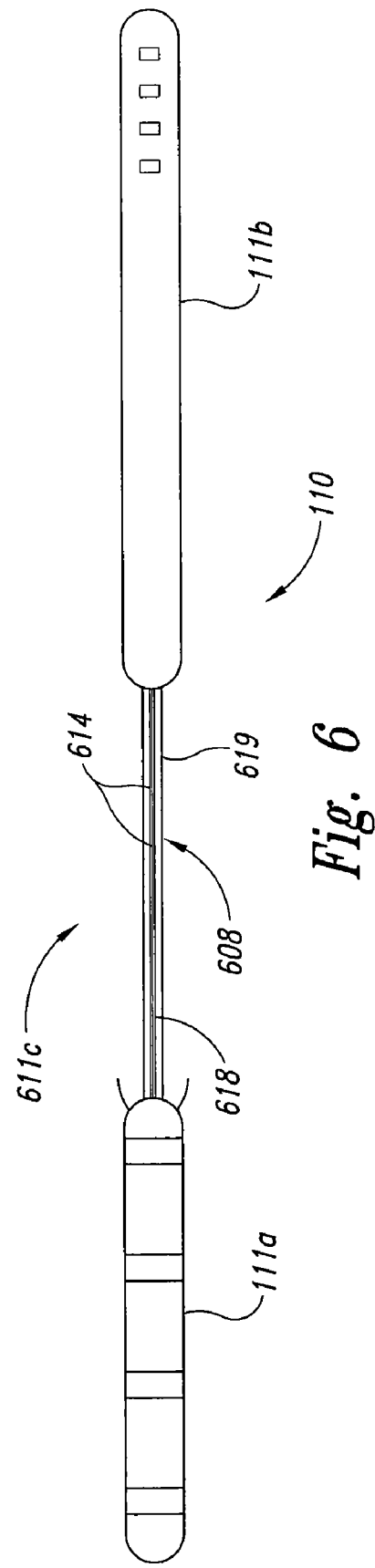
Fig. 5
Fig. 6

PERCUTANEOUS LEADS WITH LATERALLY DISPLACEABLE PORTIONS, AND ASSOCIATED SYSTEMS AND METHODS

TECHNICAL FIELD

The present disclosure is directed generally to percutaneous leads with laterally displaceable portions, and associated systems and methods.

BACKGROUND

Neurological stimulators have been developed to treat pain, movement disorders, functional disorders, spasticity, cancer, cardiac disorders, and several other medical conditions. Implantable neurological stimulation systems generally have an implantable pulse generator and one or more electrode leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes. In many cases, the SCS leads are implanted percutaneously through a large needle inserted into the epidural space, with or without the assistance of a stylet. One concern of such leads is that the leads may not remain in the desired position after being implanted. This is undesirable because, if the leads migrate from the initial implantation site, the stimulation provided by the electrodes may no longer be directed to the appropriate target tissue. Accordingly, the efficacy of the treatment can be significantly compromised.

Another type of stimulation lead is a paddle lead. Paddle leads typically have a relatively flat body with electrodes arranged on one side of the body. Paddle leads are commonly used for cortical stimulation and SCS applications. Large paddle leads are desirable because they cover more neurological structures and, in at least some cases, may be more stable and less subject to migration than cylindrical leads. However, large paddle leads are not well suited to percutaneous implantation. As a result, large paddle leads are often surgically implanted using highly invasive procedures that are costly and can lead to patient complications.

One approach to addressing the potential for lead migration is to provide structural reinforcement in one or more portions of the lead, as disclosed in U.S. Pat. No. 7,146,222. However, this approach is principally directed to brain implants, and may not be effective for implantation at other sites, including the spinal cord. Accordingly, there remains a need for improved stimulation devices that resist migration.

BRIEF DESCRIPTION OF THE DRAWINGS

FIG. 2A is a partially schematic illustration of a lead body configured in accordance with an embodiment of the disclosure.

FIG. 2B is a partially schematic, transverse cross-sectional illustration of a lead body taken substantially along line 2B-2B of FIG. 2A.

FIG. 2C is a partially schematic, transverse cross-sectional illustration of a lead body having a diameter configured in accordance with another embodiment of the disclosure FIG. 3 is a partially schematic, axial cross-sectional illustration of an embodiment of the lead body shown in FIG. 2A.

FIG. 5 is a partially schematic illustration of a lead body having an intermediate portion that includes a ribbon cable in accordance with an embodiment of the disclosure.

FIG. 6 is a partially schematic illustration of a lead body having an intermediate portion that includes a reinforced electrical link in accordance with an embodiment of the disclosure.

DETAILED DESCRIPTION

A. Overview

Figure 1:
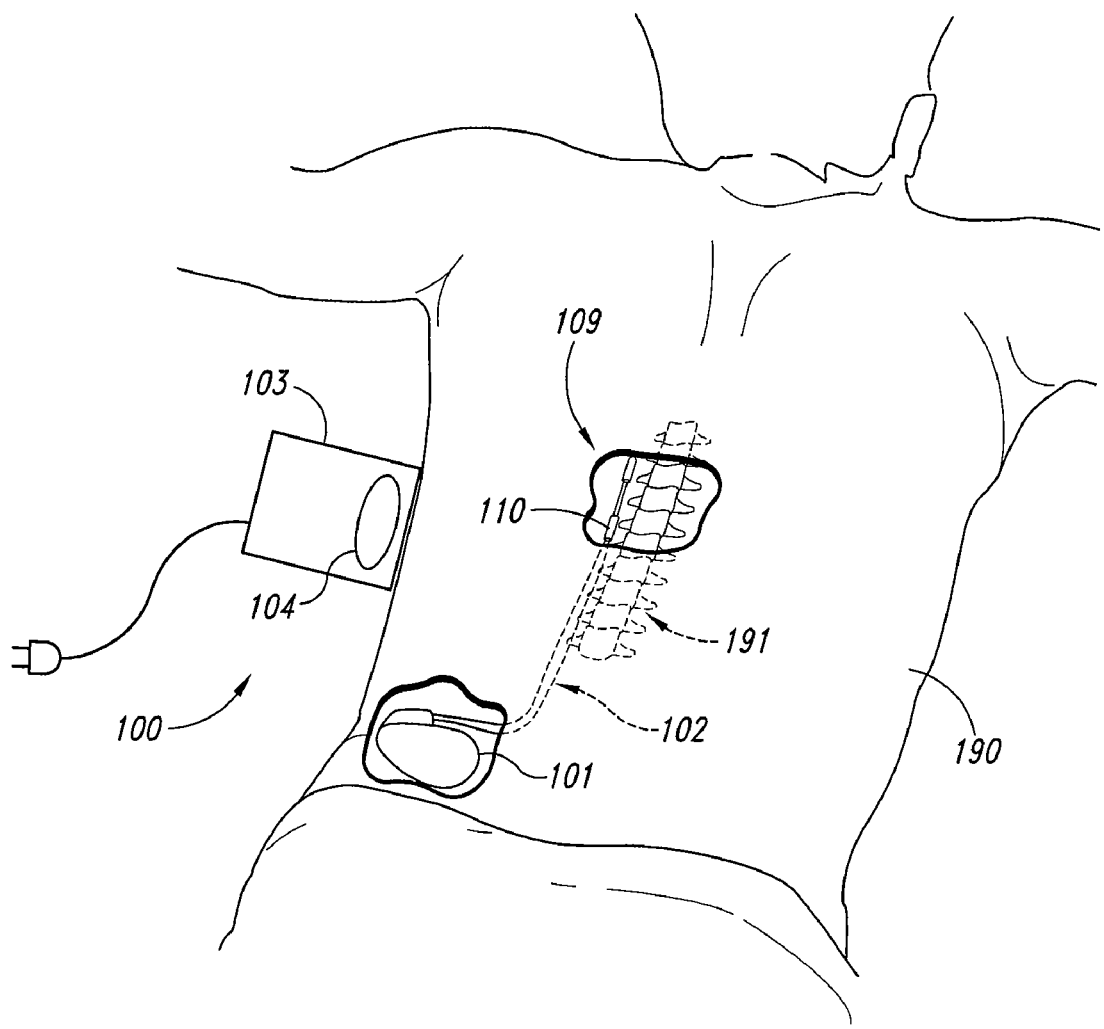
FIG. 1 is a schematic diagram of an implantable spinal stimulation system having a lead body positioned at the spine in accordance with an embodiment of the present disclosure.

Specific details of several embodiments of the disclosure are described below with reference to implantable leads for stimulating neural structures, methods for implanting leads, and methods for stimulating a target neural site of a patient. Although selected embodiments are described below with respect to stimulating the dorsal root and/or other regions of the spinal column to control pain, the leads may in some instances be used for stimulating other neurological structures, and/or other tissue (e.g., muscle tissue). Several embodiments can have configurations, components or procedures different than those described in this section, and other embodiments may eliminate particular components or procedures. A person of ordinary skill in the relevant art, therefore, will understand that the invention may have other embodiments with additional elements, and/or may have other embodiments without several of the features shown and described below with reference to FIGS. 1-7.

A patient treatment device in accordance with a particular embodiment includes a lead body having three percutaneous portions. The percutaneous portions include a first portion carrying an electrode and having a first diameter, a second portion spaced apart from the first portion and having a second diameter, and a third portion positioned between the first and second portions along a deployment axis. The third portion has a third diameter less than the first and second diameters, and a stiffness in a direction transverse to the deployment axis that is less than the stiffness of the first portion transverse to the deployment axis, and less than a stiffness of the second portion transverse to the deployment axis. Accordingly, in particular embodiments, the reduced diameter and reduced stiffness of the intermediate third portion can provide strain relief and reduces the likelihood that the first portion, which is typically located at or near the stimulation site, will become displaced from the stimulation site. For example, the intermediate portion can allow relative movement between the first portion located at the stimulation site, and the second portion, which may be spaced apart from the stimulation site. Such relative movement can occur when the patient moves (e.g., bends or twists) in a certain manner.

In particular embodiments, the third portion includes a flexible, electrical link that is coupled to the electrode and is unsupported between the first and second portions in a direction transverse to the deployment axis. The electrical link can include, for example, an insulated wire or a ribbon of insulated wires. In some cases, the third portion also includes an axial reinforcing fiber arranged along the wire(s).

In still another particular arrangement, the lead body includes a first axial aperture extending into the first portion, and a second axial aperture extending through the second portion. The delivery device can include a stylet that is removably received in both the first and second apertures. The first portion and the stylet can be releaseably coupled to each other with a bayonet fitting, and can be separated from each other via relative twisting and axial movement of the stylet relative to the first portion.

Further aspects of the disclosure are directed to methods for deploying a treatment device. A representative method includes delivering a lead body into a patient's body so that a first portion of the lead body having a first diameter and carrying an electrode is proximate to a spinal stimulation site, a second portion of the lead body having a second diameter is positioned radially outwardly from the first portion, and a third portion of the lead body is positioned between the first and second portions. The third portion can have a third diameter less than both the first and second diameters. The method can further include at least partially fixing the first portion, the second portion, or both the first and second portions to the patient's body, while allowing the third portion to accommodate relative movement between the first and second portions.

In particular embodiments, the first portion of the lead body can be positioned within the spinal canal, and the second portion of the lead body can be positioned external to the spinal canal. The electrode carried by the first portion can be located in electrical communication with dorsal root neurons, in a gutter along the spinal cord, or in a dorsal root entry zone.

B. Overview of Embodiments of Implantable Neural Stimulation Systems and Associated Methods FIG. 1 schematically illustrates a representative treatment system 100 for providing relief from chronic pain and/or other conditions, arranged relative to the general anatomy of a patient's spinal cord 191. The system 100 can include a pulse generator 101 implanted subcutaneously within a patient 190 and coupled to a lead 109. The lead 109 can include a lead body 110 that carries features for delivering therapy to the patient 190 after implantation. The pulse generator 101 can be connected directly to the lead body 110 or it can be coupled to the lead body 110 via a communication link 102. As used herein, the term lead body includes any of a number of suitable substrates and/or support members that carry devices for providing therapy signals to the patient 190. For example, the lead body 110 can include one or more electrodes or electrical contacts that direct electrical signals into the patient's tissue to provide for patient relief. In other embodiments, the lead body 110 can carry other devices that direct electrical signals and/or other types of signals to the patient 190.

The pulse generator 101 can transmit signals to the lead body 110 that up-regulate (e.g. stimulate) and/or down-regulate (e.g. block) target nerves. Accordingly, the pulse generator 101 can include a machine- (e.g., computer-) readable medium containing instructions for generating and transmitting suitable therapy signals. The pulse generator 101 and/or other elements of the system 100 can include one or more processors, memories and/or input/output devices. The pulse generator 101 can include multiple portions, e.g., for directing signals in accordance with multiple signal delivery parameters, housed in a single housing (as shown in FIG. 1), or in multiple housings. Representative signal delivery parameters are disclosed in pending U.S. Provisional Application No. 60/985,353, filed Nov. 5, 2007, assigned to the assignee of the present application, and incorporated herein by reference.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In still further embodiments, an external programmer (not shown) can communicate with the implantable pulse generator 101 via electromagnetic induction. Accordingly, a practitioner can update the therapy instructions provided by the pulse generator 101. Optionally, the patient may also have control over at least some therapy functions, e.g., starting and/or stopping the pulse generator 101.

FIG. 2A is a partially schematic, side elevation view of the lead body 110 configured in accordance with a particular embodiment. The lead body 110 can include a first or distal portion 111a, a second or proximal portion 111b, and an intermediate third portion 111c located between the first and second portions 111a, 111b. The first portion 111a can carry signal delivery electrodes 112, or other features configured to deliver therapeutic signals to the patient. The second portion 111b can include connection terminals 113 or other features configured to facilitate communication with the implantable pulse generator 101 (FIG. 1). The third portion 111c can include a link, e.g., an electrical link 108 that provides signal communication between the connection terminals 113 of the second portion 111b and the signal delivery electrodes 112 of the first portion 111a.

The first portion 111a can include signal delivery electrodes 112 that have an annular or ring shape and are exposed at the outer circumferential surface of the first portion 111a, as shown in FIG. 2A. In other embodiments, the signal delivery electrodes 112 can have other configurations, e.g., the electrodes 112 can have a flat or curved disc shape. The first portion 111a can have an overall diameter D1 which is sized to allow the first portion 111a to pass through the lumen of a delivery catheter or other delivery device. The first portion 111a can also include a first fixation device 115a to secure or at least partially secure the first portion 111a in position at a target site. In a particular embodiment, the first fixation device 115a can include one or more tines, or an annular cup that faces proximally (rightward as shown in FIG. 2A) to resist axial motion. In other embodiments, the first fixation device 115a can include other features.

The second portion 111b can include the connection terminals 113 described above, and can have an overall diameter D2. In a particular embodiment, the diameter D2 of the second portion of 111b can be approximately the same as the diameter D1 of the first portion of 111a. The second portion 111b can include a second fixation device 115b, for example, one or more sutures 106 that secure or at least partially secure the second portion 111b in position. Each of the first and second portions 111a, 111b can include rounded, convex external surfaces 105 (e.g., at the proximal end of the first portion 111a and/or at the distal end of the second portion 111b) that are exposed to patient tissue and, due to the rounded shapes of these surfaces, facilitate moving the lead body 110 in the patient's body.

The first portion 111a, the second portion 111b, and the third portion 111c can be arranged along a deployment axis A. The electrical link 108 can include one or more wires 114 connected between the signal delivery electrodes 112 at the first portion 111a and the connection terminals 113 at the second portion 111b. In an embodiment shown in FIG. 2A, each of the individual wires 114 is independently insulated, relatively thin, and movable relative to the other wires 114. Accordingly, the third portion 111c can have a stiffness transverse to the deployment axis A, (indicated by arrows T), that is less than a corresponding stiffness of the first portion 111a and/or the second portion 111b in the same direction. In a particular embodiment, the third portion 111c is less stiff (or more flexible) than both the first portion 111a and the second portion 111b. This arrangement can allow the first portion 111a and the second portion 111b to be independently displaced transversely relative to each other. For example, the third portion 111c can be flexible enough to allow the second portion 111b to move without disturbing the position of the first portion 111a. In a particular embodiment, the third portion 111c includes no structures that extend axially the length of the third portion, other than the wires 114. For example the third portion 111c need not include a shaft that disposed around the wires 114, which is unlike existing leads. An advantage of this arrangement is that it can further increase the flexibility of the third portion 111c and reduce the likelihood that motion of the second portion 111b will cause the first portion 111a to move.

In a particular embodiment, the third portion 111c has a diameter D3 that is less than the diameter D1 of the first portion 111a, and/or less than the diameter D2 of the second portion 111b. As shown in cross section in FIG. 2B, the diameter D3 of the third portion 111c can be an envelope that includes each of the wires 114 as they lie in position. Alternatively, as shown in FIG. 2C, the diameter D3 can be an effective diameter corresponding to the minimal cross-sectional area of the wires 114, assuming the wires 114 are positioned in a compact (e.g., surface-to-surface) arrangement. In either case, the diameter D3 can be significantly less than the diameters D1 and D2 to facilitate the additional flexibility of the third portion 111c relative to the first portion 111a and the second portion 111b. For example, the diameter D3 can be one half, one quarter, or less than one quarter of the diameters D1 and D2.

FIG. 3 is a cross-sectional illustration of the lead body 110 positioned within a lumen 121 of a delivery catheter 120. As shown in FIG. 3, the first portion 111a can include a first aperture 116a, and the second portion 111b can include a second aperture 116b. A delivery device 130 (e.g., a stylet) passes entirely through the second aperture 116b and into the first aperture 116a. When the third portion 111c includes wires 114, the delivery device 130 can pass alongside, around and/or through interstices between the wires 114. Accordingly, the third portion 111c in this embodiment need not include a defined, axially-extending aperture.

In operation, the catheter 120 is positioned percutaneously within the patient, and the delivery device 130 is used to push the lead body 110 through the catheter 120 and into the patient. In particular embodiments, the lead delivery device 130 can be temporarily secured to the lead body 110 during delivery, as described below with reference to FIG. 7. The delivery device 130 is then removed by withdrawing it through the first aperture 116a and the second aperture 116b, leaving the lead body 110 in place in the patient. The lead body 110 can be secured to the patient using any of the fixation devices 115a, 115b described above with reference to FIG. 2A.

Figure 4A:
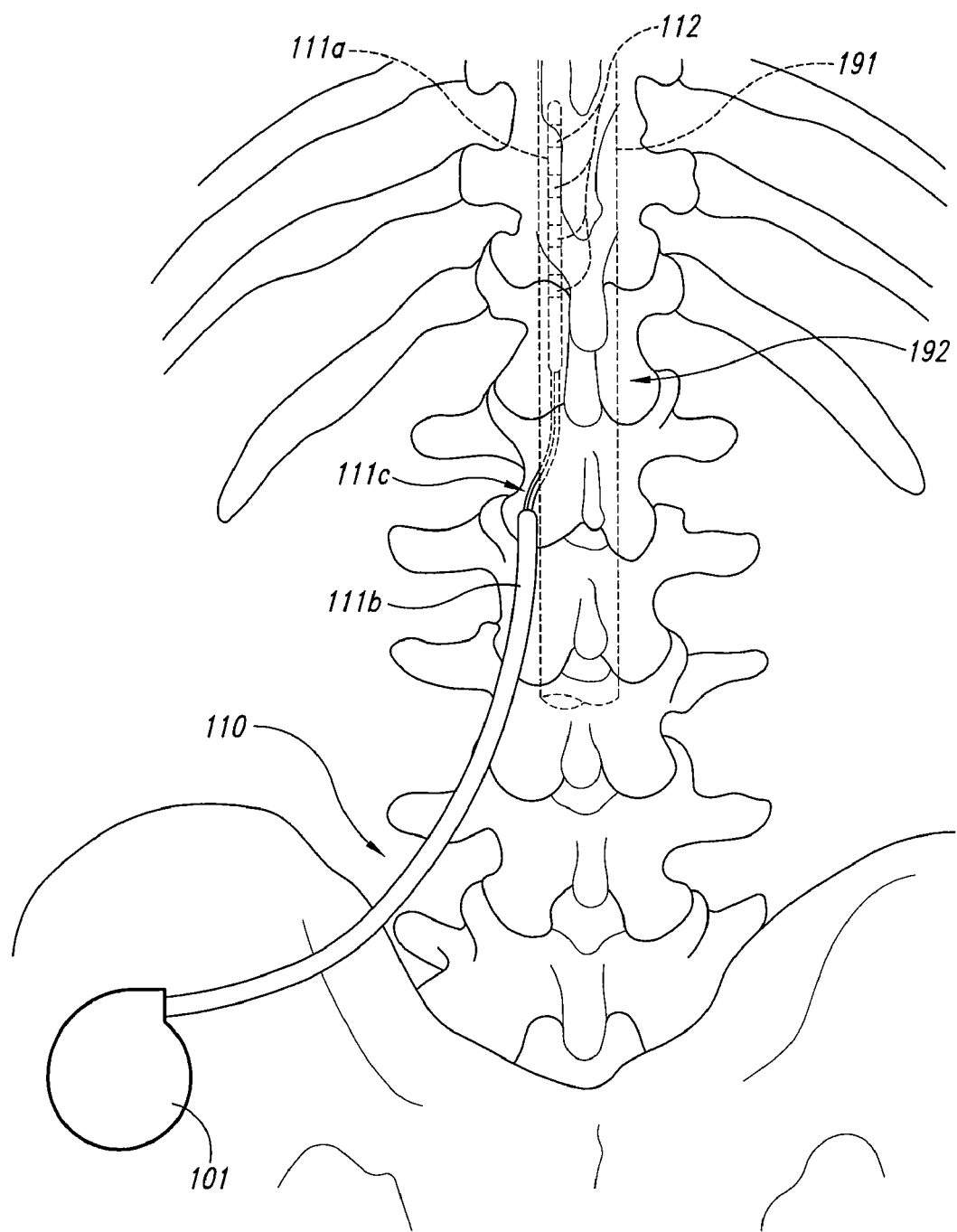
FIG. 4A is a partially schematic illustration of a lead body placed at the lumbar region of a patient's spine in accordance with an embodiment of the disclosure.

FIG. 4A is a partially schematic illustration of the lower portion of the patient's spine, illustrating the lower lumbar vertebrae. A lead body 110 in accordance with a particular embodiment is shown in a representative percutaneously-delivered position at the spinal cord 191. In this embodiment, the lead body 110 is positioned alongside the spinal cord 191, with the first portion 111a located within the spinal column 192, the second portion 111b located outside the spinal column 192, and the third portion 111c coupled between the first portion 111a and the second portion 111b. Accordingly, the first portion 111a can be positioned at a target site for delivering stimulation signals to target neural populations, and the second portion 111b can be positioned in or adjacent to muscle tissue, ligamentous tissue, and/or other tissue and secured in place. As discussed above, the second portion 111b can be electrically connected directly to a pulse generator 101, or it can be coupled to the pulse generator 101 with an intermediate communication link 102 (FIG. 1), such as an extension. The second portion 111b can be located radially (e.g., laterally) outwardly from the first portion 111a so that it is offset laterally from the spinal column 192 to facilitate securing it to non-neural tissue. The third portion 111c can flex in a lateral or radial direction to accommodate the radial offset of the second portion 111b relative to the first portion 111a. In addition, if/when the tissue adjacent the second portion 111b moves relative to the patient's spinal cord 191, as is likely to happen when the patient bends or twists, the third portion 111c can accommodate such relative movement due to its increased transverse flexibility.

The axial length of the first portion 111a can be relatively short, e.g., just long enough to support the electrodes 112 for providing the target electrical stimulation to the target neural population. The length of the first portion 111a can be less than that of conventional lead bodies so that the first portion 111a may be secured in place without being displaced by a bulky proximal portion. The isolation provided by the third portion 111c can facilitate this arrangement.

Figure 4B:
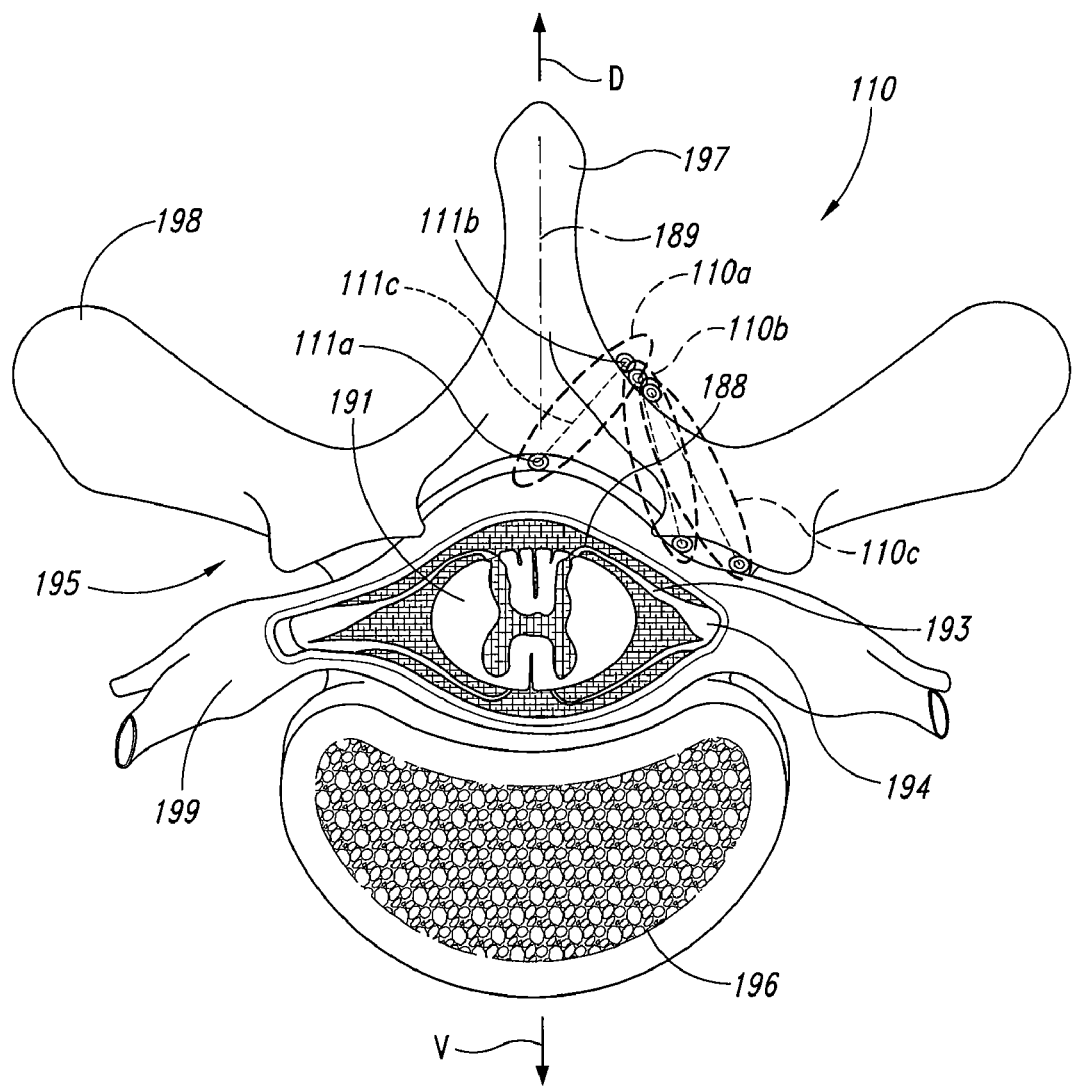
FIG. 4B is a partially schematic, cross-sectional illustration of the patient's spine illustrating representative locations of lead bodies in accordance with embodiments of the disclosure.

FIG. 4B is a cross-sectional illustration of the spinal cord 191 and an adjacent vertebra 195 (based generally on information from Crossman and Neary, "Neuroanatomy," 1995 (publ. by Churchill Livingstone)), along with selected representative locations for representative lead bodies 110 (shown as lead bodies 110a-111c) in accordance with several embodiments of the disclosure. The spinal cord 191 is located between a ventrally located vertebral body 196 and the dorsally located transverse process 198 and spinous process 197. Arrows V and D identify ventral and dorsal directions, respectively. The spinal cord 191 itself is located within the dura mater 199, which also surrounds portions of the nerves exiting the spinal cord 191, including the dorsal roots 193 and dorsal root ganglia 194. In a particular embodiment, a lead body 110a can be positioned centrally in a lateral direction (e.g., aligned with the spinal cord midline 189) to provide signals directly to the spinal cord 191. In other embodiments, the lead body can be located laterally from the midline 189. For example, the lead body can be positioned proximate to the dorsal root entry zone 188, or proximate to the dorsal root 193 (as indicated generally by lead body 110b), and/or proximate to the dorsal root ganglion 194 (as indicated by lead body 110c). Other suitable locations for the lead body 110 include the "gutter," also located laterally from the midline 189 and medially from the dorsal root ganglion 194. In general, for locations off the midline 189, at least part of the first portion 111*a* may extend outwardly in a lateral direction, rather than straight into or out of the plane of FIG. 4B. In still further embodiments, the lead bodies may have other locations proximate to the spinal cord 191 and/or proximate to other target neural populations. In yet further embodiments, devices having any of the characteristics described herein may be used to direct signals to tissues outside the patient's nervous system. In each of the foregoing embodiments, the first portion 111*a* of the lead body 110 can be positioned epidurally (or subdurally) proximate to a target neural population at the spinal cord 191 while the second portion 111*b* is positioned radially outwardly from the spinal cord 191, and while the third portion 111*c* provides a flexible coupling between the first and second portions.

FIG. 5 illustrates a lead body 110 having a third portion 511*c* that includes an electrical link 508 configured in accordance with another embodiment of the disclosure. In this particular embodiment, the electrical link 508 includes wires 514 that are not individually movable relative to each other, as was the case in the arrangement discussed above with reference to FIG. 2A. Instead, the wires 514 can be arranged in a ribbon cable 517 or other composite structure that fixes each of the wires 514 relative to each other. An expected advantage of this arrangement is that it may be easier to control the locations of the wires 514 when they are fixed relative to each other. Conversely, an advantage of the arrangement described above with reference to FIG. 2A is that the ability of individual wires 114 to move relative to each other can further increase the flexibility of the third portion 111*c* in the transverse direction T. Accordingly, the practitioner can select the arrangement expected to produce the best results for an individual patient.

FIG. 6 is a partially schematic, side elevation view of a lead body 110 having a third portion 611*c* configured in accordance with still another embodiment. In this embodiment, the third portion 611*c* includes an electrical link 608 having multiple wires 614 and a transverse flexibility controlled by one or more additional features. For example, the wires 614 can be bundled together so as not to move relative to each other, and/or can further include a reinforcing fiber 618 that further controls lateral flexibility. In addition to and/or in lieu of the reinforcing fiber 618, the third portion 611*c* can include a casing 619 that surrounds the wires 614. The casing 619 can also control lateral flexibility of the third portion 611*c*, while still providing the third portion 611*c* with greater lateral flexibility than that of either the first portion 111*a* or the second portion 111*b*. As described above with reference to FIG. 5, the practitioner can select an arrangement suitable for a particular patient based on the expected level of desired transverse flexibility.

Figure 7:
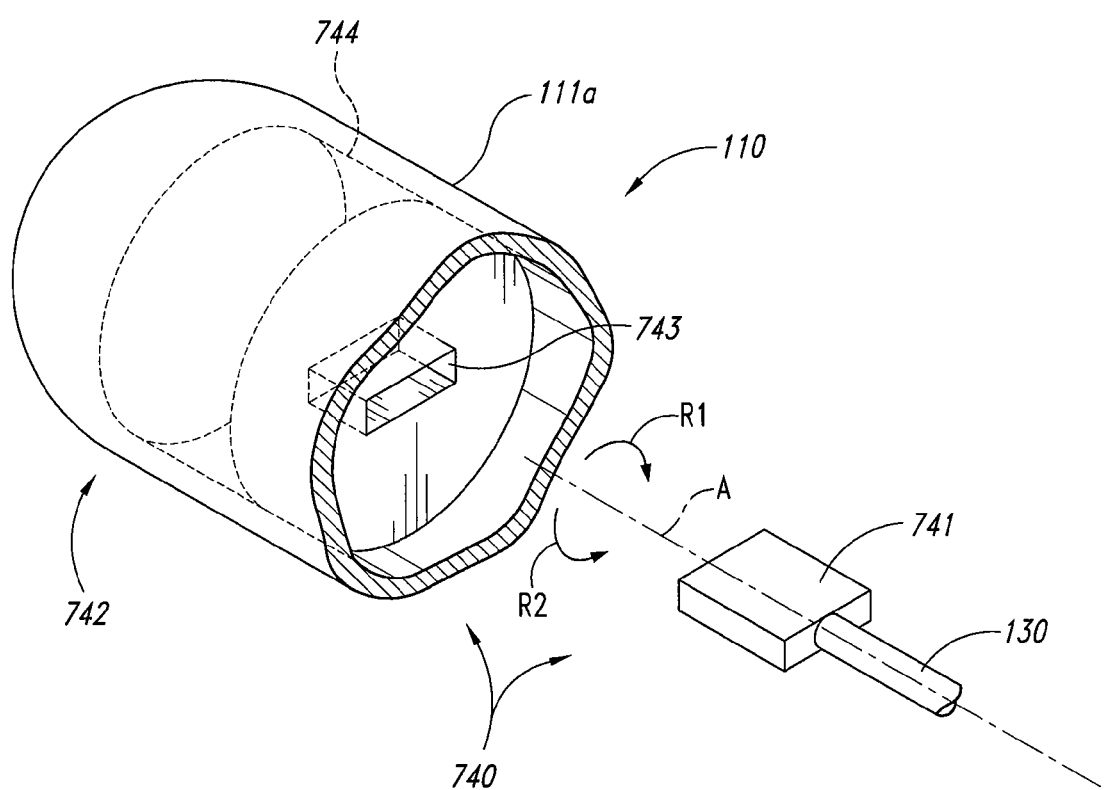
FIG. 7 is partially schematic, isometric illustration of a bayonet device for releaseably securing a delivery device to a lead body during percutaneous insertion, in accordance with an embodiment of the disclosure.

In any of the foregoing embodiments, the lead body 110 can be delivered percutaneously to the patient via a delivery device 130, as was discussed above with reference to FIG. 3. FIG. 7 is a partially schematic, isometric illustration of a particular arrangement by which the delivery device 130 can be releaseably secured to the first portion 111*a* of the lead body 110 during implantation. In particular, the arrangement can include a bayonet device 740 that facilitates the releaseable connection. The bayonet device 740 can include a bayonet receptacle 742 positioned in a distal end of the first portion 111*a*, and a bayonet fitting 741 carried by the delivery device 130. The bayonet receptacle 742 can include an entry 743 and a chamber 744 accessible via the entry 743. The entry 743 can have a slot shape or other shape that corresponds to the non-isodiametric shape of the bayonet fitting 741. The chamber 744 can have a cylindrical shape that allows the bayonet fitting 741 to be rotated about the deployment axis A once inside the chamber 744. Accordingly, in operation, the delivery device 130 can be secured to the first portion 111*a* by positioning the bayonet fitting 741 as shown in FIG. 7, inserting it through the entry 743 and into the chamber 744, and rotating the delivery device 130 relative to the first portion 111*a* as indicated by arrow R1. For example, the delivery device 130 can be rotated by 90°. In this orientation, the bayonet fitting 741 cannot be removed from the first portion 111*a* by axial motion alone. Accordingly, the delivery device 130 can be moved axially forward or backward until the first portion 111*a* has the desired axial position. Once the first portion 111*a* has the desired axial position, the practitioner can rotate the delivery device 130 in the opposite direction, as indicated by arrow R2, and withdraw the bayonet fitting 741 from the bayonet receptacle 742. An expected advantage of the foregoing arrangement when compared to conventional stylet arrangements is that it can allow the practitioner to move the first portion 111*a* both forward and backward during the positioning task, without decoupling the delivery device 130 from the first portion 111*a*.

From the foregoing, it will be appreciated that specific embodiments of the disclosure have been described herein for purposes of illustration, but that various modifications may be made without deviating from the disclosure. For example, the lead body portions 111*a*-111*c* can have other shapes that facilitate an offset and/or relative lateral movement between the first portion 111*a* and the second portion 111*b*. Certain aspects of the disclosure described in the context of particular embodiments may be combined or eliminated in other embodiments. For example, the bayonet fitting shown in FIG. 7 may be included with any of the devices shown in FIGS. 1-6. Further, while advantages associated with certain embodiments have been described in the context of those embodiments, further embodiments may also exhibit such advantages, and not all embodiments need necessarily exhibit such advantages to fall within the scope of the invention. Accordingly, the disclosure can include other embodiments not expressly shown or described above.

I claim:

1. A patient treatment device, comprising a lead body that includes:
   a first percutaneous portion carrying a plurality of electrodes and having a first aperture extending into the first percutaneous portion, the first percutaneous portion having a first diameter and a first portion of a bayonet fitting, the stylet;
   a second percutaneous portion spaced apart from the first percutaneous portion and having a second aperture extending entirely through the second percutaneous portion, the second percutaneous portion having a second diameter; and
   a third percutaneous portion positioned between the first and second portions along a deployment axis and having a third diameter less than the first and second diameters, the third portion having a stiffness in a direction transverse to the deployment axis that is less than a stiffness of the first portion transverse to the deployment axis, and less than a stiffness of the second portion transverse to the deployment axis, the third portion including multiple electrical signal paths between the second portion and the electrodes of the first portion; and
   a stylet removably received in the first and second apertures, the stylet having a second portion of the bayonet fitting and the first percutaneous portion being releasably coupled with the bayonet fitting, with the stylet being rotatable about the deployment axis and translatable along the deployment axis relative to the first percutaneous portion between a secured position and an unsecured position.

2. The device of claim 1 wherein the third diameter is less than one quarter of the first diameter, and less than one quarter of the second diameter.

3. The device of claim 1 wherein the first portion has a uniform first diameter, and wherein the electrodes are exposed around a circumference of the first portion.

4. The device of claim 1 wherein the multiple electrical signal paths are part of a flexible electrical link that is coupled to the electrodes and is unsupported between the first and second portions in a direction transverse to the deployment axis.

5. The device of claim 4 wherein the electrical link includes an insulated wire.

6. The device of claim 5, further comprising an axial reinforcing fiber arranged along the wire.

7. The device of claim 4 wherein the electrical link includes a ribbon of insulated wires.

8. The device of claim 4 wherein the second portion includes a plurality of electrical terminals, and wherein the electrical link is connected between the plurality of electrodes and the plurality of electrical terminals.

9. The device of claim 1 wherein the third portion does not include an aperture.

10. The device of claim 1 wherein the electrical signal paths of the third portion include multiple flexible electrical links, with individual electrical links coupled to corresponding individual electrodes and with the individual electrical links unsupported between the first and second portions in a direction transverse to the deployment axis, the individual electrical links being movable relative to each other between the first and second portions.

11. The device of claim 1 wherein the first portion includes a fixation device positioned to fix the first portion relative to adjacent tissue.

12. The device of claim 11 wherein the fixation device includes a tine.

13. The device of claim 11 wherein the fixation device includes a proximally-facing cup positioned annularly around the first portion and extending radially outwardly from the first portion.

14. The device of claim 1 wherein the second portion includes a fixation device positioned to fix the second portion relative to adjacent tissue.

15. The device of claim 14 wherein the fixation device includes a suture.

16. A patient treatment device, comprising a lead body that includes:
   a first percutaneous portion carrying multiple electrodes and having a first aperture extending into the first percutaneous portion and a first portion of a bayonet fitting, the stylet;
   a second percutaneous portion spaced apart from the first percutaneous portion, carrying multiple terminals and having a second aperture extending entirely through the second percutaneous portion;
   a third percutaneous portion positioned between the first and second portions along a deployment axis, the third portion having a stiffness in a direction transverse to the deployment axis that is less than a stiffness of the first portion transverse to the deployment axis, and less than a stiffness of the second portion transverse to the deployment axis, the third portion including multiple individual wires coupled between individual electrodes and corresponding terminals, the individual wires being movable relative to each other at the third portion, wherein the third portion does not include a shaft disposed around the individual wires; and
   a stylet removably received in the first and second apertures, the stylet having a second portion of the bayonet fitting and the first percutaneous portion being releasably coupled with a bayonet fitting, with the stylet being rotatable about the deployment axis and translatable along the deployment axis relative to the first percutaneous portion between a secured position and an unsecured position.

17. The device of claim 16 wherein:
   the first portion has a generally uniform first diameter;
   the electrodes are generally cylindrical in shape and aligned along the deployment axis;
   the second portion has a second generally uniform diameter equal to or approximately equal to the first diameter, and wherein the third portion has a third diameter less than both the first and second diameters.

18. The device of claim 16 wherein the first portion has a first convex rounded surface that intersects the deployment axis at the proximal end of the first portion, and wherein the second portion has a second convex rounded surface that intersects the deployment axis at the distal end of the second portion, the first and second convex rounded surfaces being positioned to be exposed to patient tissue after implantation.

19. A patient treatment device, comprising a lead body that includes:
   a first percutaneous portion carrying multiple electrodes and having a first aperture extending into the first percutaneous portion, the first percutaneous portion having a first diameter a first portion of a bayonet fitting, the stylet and including a first tissue fixation element;
   a second percutaneous portion spaced apart from the first percutaneous portion, carrying multiple terminals and having a second aperture extending entirely through the second percutaneous portion, the second percutaneous portion having a second diameter and including a second tissue fixation element; and
   a third percutaneous portion positioned between the first and second portions along a deployment axis, the third portion having a third diameter less than the first diameter and less than the second diameter, the third portion having a stiffness in a direction transverse to the deployment axis that is less than a stiffness of the first portion transverse to the deployment axis, and less than a stiffness of the second portion transverse to the deployment axis, the third portion including multiple individual wires coupled between individual electrodes and corresponding terminals, the individual wires being movable relative to each other at the third portion, wherein the third portion does not include a shaft disposed around the individual wires; and
   a delivery stylet extending through the second aperture and into the first aperture, with the individual wires arranged externally to the stylet between the first and second portions, the stylet having a second portion of the bayonet fitting and the first percutaneous portion being releasably coupled with the bayonet fitting, with the stylet being rotatable about the deployment axis and translatable along the deployment axis relative to the first percutaneous portion between a secured position and an unsecured position.

\* \* \* \* \*

UNITED STATES PATENT AND TRADEMARK OFFICE
CERTIFICATE OF CORRECTION

| | | |
|---|---|---|
| PATENT NO. | : 8,108,052 B2 | Page 1 of 1 |
| APPLICATION NO. | : 12/129078 | |
| DATED | : January 31, 2012 | |
| INVENTOR(S) | : C. L. Boling | |

It is certified that error appears in the above-identified patent and that said Letters Patent is hereby corrected as shown below:

On page 2, in column 2, under "Other Publications", line 1, delete "InterStrim" and insert -- InterStim --, therefor.

In column 1, line 67, after "disclosure" insert -- . --.

In column 2, line 18, delete "releaseably" and insert -- releasably --, therefor.

In column 3, line 9, delete "releaseably" and insert -- releasably --, therefor.

In column 6, line 50, delete "110a-111c)" and insert -- 110a-110c) --, therefor.

In column 7, line 59, delete "releaseably" and insert -- releasably --, therefor.

In column 7, line 62, delete "releaseable" and insert -- releasable --, therefor.

In column 8, line 49, in claim 1, delete ", the stylet".

In column 8, line 67, in claim 1, after "fitting", insert -- , the stylet --.

In column 9, line 55-56, in claim 16, delete ", the stylet".

In column 10, line 8, in claim 16, after "fitting", insert -- , the stylet --.

In column 10, line 9, in claim 16, delete "with a" and insert -- with the --, therefor.

In column 10, line 34, in claim 19, after "diameter", insert -- and --.

In column 10, line 34-35, in claim 19, delete ", the stylet".

In column 10, line 60, in claim 19, after "fitting", insert -- , the stylet --.

Signed and Sealed this
Twenty-sixth Day of June, 2012

David J. Kappos
*Director of the United States Patent and Trademark Office*